(12) United States Patent
Herring

(10) Patent No.: US 12,303,234 B2
(45) Date of Patent: May 20, 2025

(54) DIFFUSE ACOUSTIC CONFOCAL IMAGER

(71) Applicant: Rodney Herring, Victoria (CA)

(72) Inventor: Rodney Herring, Victoria (CA)

(*) Notice: Subject to any disclaimer, the term of this patent is extended or adjusted under 35 U.S.C. 154(b) by 974 days.

(21) Appl. No.: 15/650,633

(22) Filed: Jul. 14, 2017

(65) Prior Publication Data

US 2017/0311804 A1   Nov. 2, 2017

Related U.S. Application Data

(63) Continuation-in-part of application No. PCT/IB2016/050109, filed on Jan. 11, 2016.
(Continued)

(51) Int. Cl.
*A61B 8/14* (2006.01)
*A61B 5/00* (2006.01)
(Continued)

(52) U.S. Cl.
CPC .............. *A61B 5/0068* (2013.01); *A61B 8/08* (2013.01); *A61B 8/15* (2013.01); *A61B 8/4444* (2013.01); *A61B 8/4461* (2013.01); *A61B 8/483* (2013.01); *A61B 8/5207* (2013.01); *A61B 18/20* (2013.01); *A61N 7/02* (2013.01); *G01N 29/0681* (2013.01);
(Continued)

(58) Field of Classification Search
CPC ............. A61B 8/085; A61B 18/20; A61B 2018/00595; A61B 5/0068; A61B 8/08; A61B 8/0808; A61B 8/12; A61B 8/145; A61B 8/15; A61B 8/40; A61B 8/4218; A61B 8/4281; A61B 8/4444; A61B 8/4461; A61B 8/4477; A61B 8/4494; A61B 8/483; A61B 8/5207; A61B 8/5223; A61B 8/5269; A61N 2007/0004; A61N 7/02

See application file for complete search history.

(56) References Cited

U.S. PATENT DOCUMENTS

2002/0138000 A1*  9/2002  Rather ............... A61B 8/15
                                               600/407
2004/0059265 A1   3/2004  Candy et al.
(Continued)

OTHER PUBLICATIONS

International Search Report and Written Opinion issued on May 3, 2016, in Patent Application No. PCT/IB2016/050109 (13 Pages).

*Primary Examiner* — Christopher L Cook
(74) *Attorney, Agent, or Firm* — Baumgartner Patent Law; Marc Baumgartner

(57) ABSTRACT

A diffuse acoustic confocal imager device for use with a data analyzer for providing a three dimensional and state information on an object based on an at least one phase image, the device comprising a coherent acoustic source for producing an acoustic confocal beam ranging from about 0.5 megahertz to about 100 megahertz, an acoustic coherent beam focuser for focusing the acoustic coherent beam to a virtual source, an acoustic detector for detecting an at least one diffusely scattered beam from the virtual source and a vector network analyzer, which is for measuring a phase of the acoustic confocal beam and a phase of the at least one diffusely scattered beam to provide the at least one phase image, the vector network analyzer in electronic communication with each of the coherent acoustic source and the acoustic detector. A method of detecting and treating diseases such as prostate cancer and ovarian cancer is also provided.

10 Claims, 13 Drawing Sheets

Related U.S. Application Data

(60) Provisional application No. 62/103,882, filed on Jan. 15, 2015.

(51) Int. Cl.
| | |
|---|---|
| *A61B 8/00* | (2006.01) |
| *A61B 8/08* | (2006.01) |
| *A61B 8/15* | (2006.01) |
| *A61B 18/20* | (2006.01) |
| *A61N 7/02* | (2006.01) |
| *G01N 29/06* | (2006.01) |
| *G01S 7/52* | (2006.01) |
| *G01S 15/89* | (2006.01) |
| *A61B 8/12* | (2006.01) |
| *A61B 18/00* | (2006.01) |
| *A61N 7/00* | (2006.01) |

(52) U.S. Cl.
CPC ...... *G01S 7/52036* (2013.01); *G01S 7/52079* (2013.01); *G01S 15/8913* (2013.01); *G01S 15/8925* (2013.01); *G01S 15/8993* (2013.01); *A61B 8/085* (2013.01); *A61B 8/12* (2013.01); *A61B 2018/00595* (2013.01); *A61N 2007/0004* (2013.01); *G01S 15/8956* (2013.01)

(56) References Cited

U.S. PATENT DOCUMENTS

| | | |
|---|---|---|
| 2007/0171366 A1 | 7/2007 | Su et al. |
| 2007/0263226 A1 | 11/2007 | Kurtz et al. |
| 2008/0177183 A1 | 7/2008 | Courtney et al. |
| 2008/0242992 A1 | 10/2008 | Criton |
| 2011/0092817 A1* | 4/2011 | Cloutier .............. G01S 7/52036 600/437 |
| 2011/0141481 A1* | 6/2011 | Herring .............. G01N 29/0681 356/511 |
| 2016/0114193 A1* | 4/2016 | Prus ..................... B06B 1/0662 367/137 |

* cited by examiner

DIFFUSE ACOUSTIC CONFOCAL IMAGER

CROSS REFERENCE TO RELATED APPLICATIONS

This application is a Continuation-in-Part of International Application PCT/IB2016/050109, filed Jan. 11, 2016, and claims the benefit of U.S. Provisional Patent Application No. 62/103,882, filed Jan. 15, 2015. The above-identified priority patent applications are incorporated herein by reference in their entirety.

FIELD

The present technology relates to a diffuse acoustic confocal imager. Additionally, this technology relates to acoustic confocal imaging, especially with regard to methods of using coherent acoustic beams pulsed or continuous in the diagnosis and treatment of tumours and related diseases.

BACKGROUND

The use of beams of radiation to obtain information about an object by detecting the amplitude or phase of the beam is well known for scientific and medical purposes. For example, the phase information of a beam that passes through an object can provide information on the object's temperature, composition, magnetic field or electrostatic field, whereas amplitude measurements can provide information on the opaqueness or density of the object. The beams are comprised of waves of radiation, where a wave, Φ, can be described as having both an amplitude, A, and phase, Θ, described mathematically as, $$\Phi = A\exp(\Theta) \quad \quad 1)$$

The information obtained from the method depends on whether it is detecting the amplitude or both the amplitude and phase of a beam's wave. If the method measures only a beam's amplitude, as is the case for X-ray, only density differences in the object are reported. This is a limitation of the technology as it does not provide information such as an object's temperature, composition, elasticity, strain field, magnetic or electrostatic fields. An additional disadvantage of a number of imaging techniques such as X-ray imaging methods is the strength of radiation employed. When used in diagnosis, the levels employed may have the potential to damage cells in the body.

Acoustic microscopes including Ultrasound are now widely used to image the inside of the body such as the fetus in the womb and blood flow in arties and veins. These microscopes measure the intensity of the acoustic beam reflected off surfaces such as bones and interfaces such as the interface, between the embryonic fluid and fetus. These microscopes cannot measure the intensity and phase of the beam passing through or reflected from soft tissue such as muscles or embryonic fluid. These microscopes also cannot measure temperature or composition as they only use the intensity of the acoustic beams and not the phase of the acoustic beams. Hence the images are not suitable for providing information other than that information that pertains to surfaces or interfaces. A further deficiency of these microscopes is that the image produced has a significant amount of background intensity caused by the diffuse scattering of beams. Taking as an example, a prostate gland, an ultrasound image poorly identifies the interface between the prostate and other tissue and can also identify the urethra, however, it cannot identify any abnormalities within the prostate.

Another method that measures a beam's amplitude is confocal microscopy. Confocal scanning laser microscopes were developed in the 1980s for seeing three-dimensional objects. Confocal scanning laser microscopy uses a laser beam passing through an object to create a three-dimensional amplitude image of the object by detecting the amplitude of the beam through a pinhole aperture placed confocal with a point on a focal plane of the object.

Confocal microscopes have now found widespread applications in the materials, biological, and medical sciences. As a diagnostic tool, confocal microscopes are limited to detecting only thin tissue and the density differences of objects, which produce amplitude differences of the detected beam. The beams cannot penetrate far in to tissues and other materials. They do not measure the object's phase information. Hence, confocal microscopes cannot measure an object's composition or temperature.

If the method measures changes in the phase of a beam, then information can be provided about the object's temperature and composition. Acoustic beams can be used for this. The phase of acoustic beams are modified by an object's refractive index, where the refractive index is dependent on the object's temperature and composition and is a measure of the acoustic beam's speed of sound.

The absolute phase of an object can be measured using a Confocal Scanning Holography Microscope, as described in U.S. Pat. No. 7,639,365. This approach cannot be used to image the inside of the human body as laser beams do not readily pass through the human body.

The relative phase of an object can be measured using an Acoustic Confocal interferometry Microscope, as described in U.S. Pat. No. 8,485,034. This approach requires an interference beam and a complex arrangement of mirrors and prisms and is not suitable for imaging the inside of the human body because of the geometric constraints.

Standard interferometry microscopes, standard holography microscopes, and standard holographic interferometry microscopes have been used to measure both the phase and the amplitude of objects, giving important information of objects such as their density, composition and temperature. These microscopes create a three dimensional amplitude image and phase image of the object by measuring both the phase and the amplitude. As they are light microscopes the three-dimensional information measured from these microscopes comes only from the surface of the object and not at points within the object. In all cases, a reference beam and an object beam are used to collect data that results in the creation of the images. This limits the use of these microscopes to collecting data from or about surfaces of objects. In medical diagnosis they would therefore be potentially useful for diseases of the skin, but not for diseases of internal tissues or organs.

Other means able to measure the amplitude and phase of objects using an acoustic beam is spatially-filtered transmission ultrasound phase imaging as disclosed in U.S. Pat. Nos. 6,679,846, 6,436,046, 6,132,375 and 6,193,663. Spatially-filtered transmission ultrasound phase imaging involves measuring the amplitude and phase of an emitted beam and then again measuring the amplitude and phase of the acoustic beam after it passes through the object upon its arrival at a detector. The difference in amplitude and phase is attributed to the object. From the sound source, the beam diffusely scatters outward leading to background scatter that is not wanted. Within or around this background scatter will be the image of interest. That image is representative of the interfaces of the object being imaged. It does not represent a three dimensional image, nor can it locate diseased tissue within the tissue or organ of interest. Similarly, in materials, it cannot provide a three dimensional image nor can it show a different material within the material or a region having different physical characteristics within the material, unless there is an interface, such as the interface between a liquid and a solid.

It would be advantageous to provide a device, system and method that can detect both the amplitude and phase of a beam. Such a device, system and method would be able to provide information on the object's density, temperature, composition, elasticity, strain field, magnetic or electrostatic fields. This is of great significance in the medical field, as of being able to obtain information on density, temperature, and composition allows one to be able to potentially diagnose, treat and assess effectiveness of treatments for diseases such as cancer. Ideally, the device would be suitable for being hand-held, with a variety of different shaped detector holders for application to different parts of the body, for example, but not limited to the prostate, breast, head, and skin.

Examples of an application where the measurement of temperature arid composition is important include medical diagnostics aimed at understanding the function of organs, tissue and diseased regions in the body. Presently medical researchers do not have good means to non-invasively measure the internal temperature and composition of the body. It is an object of the present technology to provide such capabilities.

What is needed is a system that utilizes a coherent beam that can be focused to a probe, which then acts as a virtual source of diffusely scattered beams, which in turn could be detected by the detector of the system and processed into meaningful data. Such a system would preferably provide the capability of detecting differences between materials, such as differences between healthy and diseased tissues, such as density, temperature and compositional differences. More preferably, the same system would allow for treatment of the diseased tissue. While the application of the technology would preferably be in the diagnosis and treatment of disease, it would also be preferably if it could be applied more broadly to detection of different materials or different states of materials in a structure or material.

SUMMARY

The present technology provides a system that utilizes a coherent beam that is focused to a probe. That probe then functions as a virtual source of diffusely scattered beams that radiate outward randomly from the probe. Some diffusely scattered beams are detected by a detector and the output from the detector is sent to a processor for processing into meaningful data using mathematical formulae. Hence, this system utilizes the diffusely scattered beams that are undesirable in Ultrasound and that interfere with the clarity of the image, to create images that identify differences between materials, such as differences between tumours and healthy tissue including density differences, temperature differences, and compositional differences. The significance of this is that a three dimensional image can be obtained of, for example a tumour or diseased state within a healthy tissue. Similarly, in non-medical applications, three dimensional images can be obtained of any structure within another medium, or a part of the same medium in a different physical state than that of the remainder of the medium.

Not only can the three dimensional image of a tumour within a tissue be provided, information about that tumour can also be provided. The speed of sound can be correlated to the type of tumour, the stage of development of the tumour and to the temperature of the tumour.

The same system can be used to treat the tumour or disease state by increasing the beam strength and dwell time either from all the emitters, or a select number of emitters or in pulses. Dwell time for imaging and diagnostics is short, for example, around 1 second or less (this would be a low dwell time), whereas dwell time for treatment could be 100 to 100s of seconds (this would be a high dwell time), for example. Without being bound to theory, the increased beam strength provides a shock wave, sometimes referred to as shock wave lithotripsy, where an externally applied acoustic pulse is focused onto an internal object such as a kidney stone to break it into tiny pieces. The increased beam strength and dwell time increases the temperature of the target region. An increase of 5 to 7 C is all that is required to kill cells. As the emitters also function as the detectors, information about the temperature of the tumour can then be used to direct treatment: of the tumour during the treatment. This is because the temperature of the tumour changes as it is broken up by the beam and also because the temperature of the tumour changes with changes in the health of the tumour. Physical disruption of the tumour allows for chemotherapy to be effective in treatment of tumours and other disease states where a restriction of blood flow is caused by the tumour or disease state. Once the tumour is broken, the blood containing the chemicals can flow and enter into the target tissue.

Another advantage of the system providing information about the temperature of the tumour or diseased tissue is that additional therapies can be employed which are not normally employed. For example, far infrared is able to penetrate tissues and to heat the target tissues, however, it presently is not used as it requires very careful monitoring of the temperature of the target tissue. The system of the present technology provides that capability, thereby allowing use of far infrared in treatments, either alone, or in combination with diffuse acoustic confocal imaging as an additional heat source.

As the system can report on the state of the tumour or the disease state, one can determine when the treatments have been successful in treating the condition.

Unlike existing technologies, the present technology can be used to first non-invasively image diseased tissue, diagnose type and state of diseased tissue, then immediately treat the disease state without having images read, a diagnosis provided, and a treatment subsequently administered. The treatment can commence immediately upon identifying the disease state, with the equipment remaining in place on or in the patient. Similarly, the effectiveness of the treatment can be monitored at the same time as the treatment is being administered.

While the focus of the technology is the identification, characterization, diagnosis, treatment and monitoring of the treatments for disease states in the body, the technology is also suited to any application wherein differences in states and conditions between materials or within materials is needing to be determined.

In one embodiment, a diffuse acoustic confocal imager device is provided for use with a data analyzer for providing a three dimensional and state information on an object based on an at least one phase image, the device comprising a coherent acoustic source for producing an acoustic confocal beam ranging from about 0.5 megahertz to about 100 megahertz, an acoustic coherent beam focuser for focusing the acoustic coherent beam to a virtual source, an acoustic detector for detecting an at least one diffusely scattered beam from the virtual source and a vector network analyzer, which is for measuring a phase of the acoustic confocal beam and a phase of the at least one diffusely scattered beam to provide the at least one phase image, the vector network analyzer in electronic communication with each of the coherent acoustic source and the acoustic detector.

In the device, the one or two-dimensional acoustic array detector may include a spatial aperture.

In the device, the coherent acoustic source, the acoustic coherent beam focuser and the acoustic detector may be integrated into a unit.

In the device, the unit may include: a housing for housing the coherent acoustic source and the acoustic coherent beam focuser; and at least one adjustable arm attached to the housing for retaining at least one acoustic detector.

The device may further comprise at least one laser emitter positioned to emit a beam at the acoustic coherent beam focuser.

In the device, the laser emitter may be an infrared laser for treating and a helium-neon laser emitter for suturing.

The device may be for imaging a prostate of a patient, wherein the unit includes a platform, the acoustic detector seated upon the platform, the adjustable arm attached to the platform and extending between the platform and the housing.

The device may further comprise a source actuator and a detector actuator.

The device may be for imaging an ovary of a patient, wherein the unit includes two adjustable arms extending from the housing, each to a distal end, each retaining an acoustic detector proximate the distal end.

In another embodiment, a method of imaging a tissue using a diffuse acoustic confocal imager device, is provided based on an at least one phase image, the method comprising emitting an acoustic confocal beam of about 0.5 to about 100 megahertz from a coherent acoustic source, focusing the acoustic confocal beam to a virtual source in the tissue, scanning the tissue with the virtual source at a low dwell time, detecting a plurality of diffusely scattered beams from the virtual source with an acoustic detector, measuring a phase of the acoustic confocal beam and a phase of at least one of the plurality of diffusely scattered beams to provide the at least one phase image of the tissue.

The method may further comprise analyzing the phase image to diagnose a disease in the tissue.

The method may further comprise treating the disease in the tissue immediately upon diagnosing the disease.

The method may further comprise treating the disease in the tissue by increasing the dwell time to a high dwell time.

The method may further comprise providing a laser emitter and treating the disease in the tissue by focusing a laser beam from the laser emitter to a virtual source on the disease.

In the method, the laser beam may be an infrared laser beam.

In yet another embodiment, a method of imaging a prostate, based on an at least one phase image is provided, the method comprising utilizing the diffuse acoustic confocal imager device described above, emitting an acoustic confocal beam of about 0.5 to about 100 megahertz, focusing the acoustic confocal beam to a virtual source in the tissue, scanning the prostate with the virtual source at a low dwell time, detecting a plurality of diffusely scattered beams from the virtual source, measuring a phase of the acoustic confocal beam and a phase of at least one of the plurality of diffusely scattered beams to provide the at least one phase image.

The method may further comprise analyzing the at least one phase image, to diagnose a disease in the prostate.

The method may further comprise treating the disease in the tissue by focusing laser beam from an infrared laser beam to a virtual source and suturing by focusing a helium-neon laser emitter to a virtual source on the prostate.

In yet another embodiment, a method of imaging an ovary, based on an at least one phase image is provided, the method comprising utilizing the diffuse acoustic confocal imager device described above, emitting an acoustic confocal beam of about 0.5 to about 100 megahertz, focusing the acoustic confocal beam to a virtual source in the tissue, scanning the ovary with the virtual source at a low dwell time, detecting a plurality of diffusely scattered beams from the virtual source, measuring a phase of the acoustic confocal beam and a phase of at least one of the plurality of diffusely scattered beams to provide the at least one phase image.

The method may further comprise analyzing the at least one phase image, to diagnose a disease in the ovary.

The method may further comprise treating the disease in the ovary by focusing laser beam from an infrared laser beam to a virtual source and suturing by focusing a helium-neon laser emitter to a virtual source on the ovary.

BRIEF DESCRIPTION OF THE DRAWINGS

The present technology will be described in conjunction with the drawings in which.

DESCRIPTION

Figure 1:
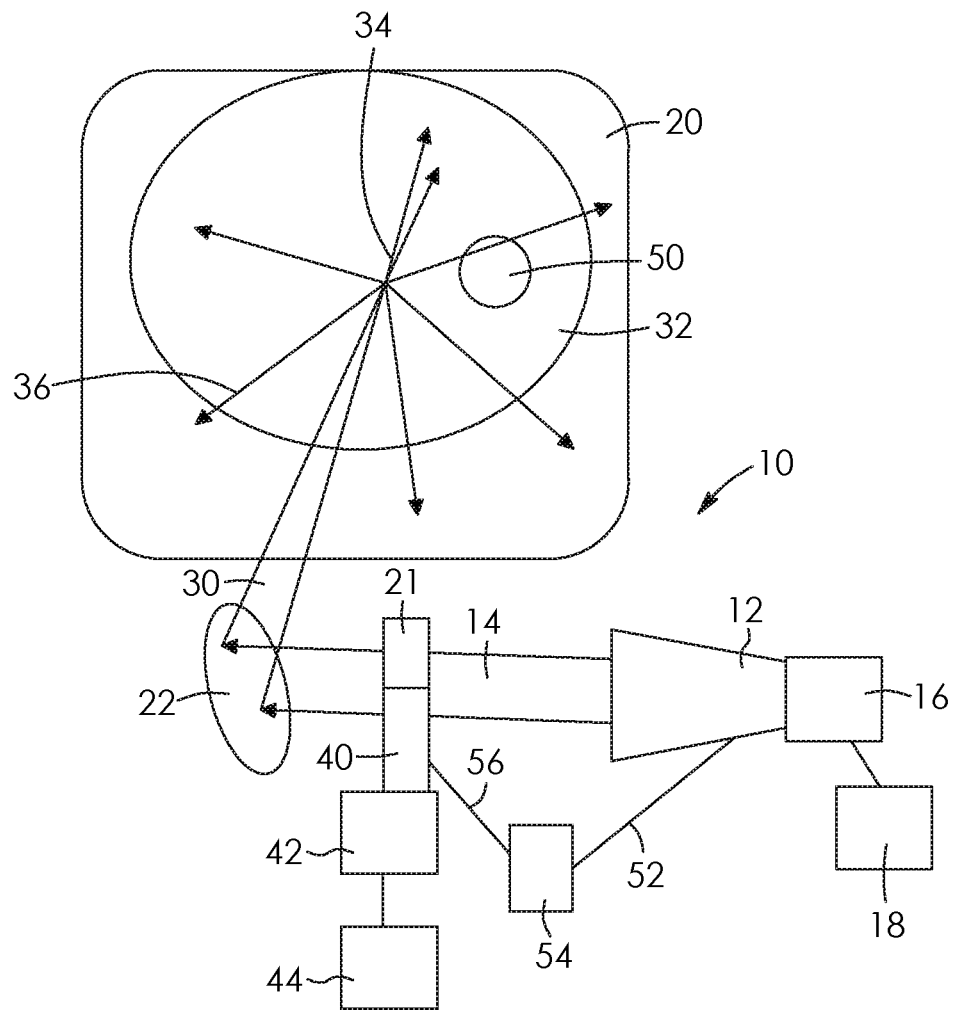
FIG. 1 is a Diffuse Acoustic Confocal Imager in accordance with a first embodiment of the technology.

Except as otherwise expressly provided, the following rules of interpretation apply to this specification (written description, claims and drawings): (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (e) descriptive headings are for convenience only and shall not control or affect the meaning or construction of any part of the specification; and (f) "or" and "any" are not exclusive and "include" and "including" are not limiting. Further, the terms "comprising," "having," "including," and "containing" are to be construed as open ended terms (i.e., meaning "including, but not limited to,") unless otherwise noted.

To the extent necessary to provide descriptive support, the subject matter and/or text of the appended claims is incorporated herein by reference in their entirety.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

Definitions

In the context of the present technology, "immediately" means that the device remains in situ while the diagnosis is made and treatment ensues. There is no need to remove the device, determine a diagnosis and then replace the device to conduct the treatment.

In the context of the present technology, shock wave lithotripsy is an externally applied acoustic pulse that is focused onto a stone to ablate it by fracturing it into small fragments.

Overview

A Diffuse Acoustic Confocal Imager (DACI) for obtaining an acoustic beam from points around, on the surfaces and inside objects that are transparent to the acoustic beam is provided for the three dimensional measurement of the amplitudes and phases of the acoustic beam intensity that is scattered from the object. A focusing lens within the optical system produces a convergent beam from the emitted coherent acoustic beam. The convergent beam is focused to a point forming a virtual source. The virtual source is scanned around, on the surfaces and inside acoustically transparent objects. A detector is placed confocal to the focused virtual source. The detector detects the beams scattered by the object from the focused virtual source. The convergence angle of the focused beam onto the object defines the three-dimensional volume of the object being measured. Each scattered beam from the focused virtual source is equivalent to an equation, providing the amplitude and phase information of the scattered beam having interacted with the part of the object given by the focused virtual source onto the object. "N" number of intensity measurements of the object are taken by the DACI and they are used to solve for "N" number of three-dimensional points describing the three-dimensional object. From the phase information obtained from the intensity measurements, the refraction index of the object, n, can be determined, which is defined as the ratio of the speed of sound (that is, the speed of the acoustic beam) in air, $c_{air}$, to the speed of sound in the object, c, for each point describing the three dimensional object. That is, $$n = c_{air}/c$$

The refractive index of the object can be used to determine the object's state, such as its temperature and/or composition.

DETAILED DESCRIPTION

FIG. 1 shows the illustration of the diffuse acoustic confocal Imager, generally referred to as 10 according to a first embodiment of the present technology. A coherent acoustic source 12 such as a coherent acoustic emitter emits a coherent acoustic beam 14. The coherent acoustic source 12 can be manually moved or can be moved with a source actuator 16 that is in mechanical communication with the coherent acoustic source 12. The source actuator 16 is preferably controlled by a processor 18, configured to direct the source actuator 16 to cause the coherent acoustic source 12 to scan the coherent acoustic beam 14 over the tissue or organ or object material 20. The coherent acoustic source 12 provides a coherent acoustic beam 14 with a beam frequency between and including about 0.5 megahertz and about 100 megahertz for obtaining information including one or more of density, temperature, composition, elasticity, or strain field in a mammalian body.

The coherent acoustic beam 14 has a large cross sectional area, typically on the order of a centimeter or a few centimeters. The coherent acoustic beam 14 passes through a spatial filter 21 to a focusing mirror or lens 22 where it is reflected by a curved surface and focused into a convergent beam 30 that penetrates the object medium 20 that transmits the convergent beam 30 into a first object, structure, medium or different physical state of the material or medium 32 in the object medium 20. The convergent beam 30 converges and is focused to a virtual source 34 at the point of cross-over. From the virtual source 34, the incoming convergent beam 30 beam is scattered in all directions three-dimensionally. The scattered beams 36 pass out of the first object 32 and the object medium 20 and are detected by an acoustic detector 40. The acoustic detector 40 is focused on the virtual source 34. The acoustic detector 40 can move to collect scattered beams 36 having a range of angular directions as indicated in FIG. 1. A detector actuator 42 is in mechanical communication with the acoustic detector 40 and is under control of a processor 44 that is in electronic communication with the detector actuator 42. The scattered beams 36 contain information about the object medium 20 and the first object 32 and are commonly referred to as the object beams. The resulting information carried by the scattered beams 36 is analyzed to determine its amplitude and phase according to techniques known in the art.

In order for the entire first object 32 to be observed, the virtual source 34 scans outside and inside the first object 32 by pivoting the focusing mirror 22 and the acoustic detector 40. Scanning of the first object 32 is also achieved by either shifting the first object 20 or shifting the microscope 10. By this means, a second object(s) 50 within the first object 32 can be imaged using the amplitude and phase information provided by the scattered beams 36 collected by the acoustic detector 40. A first wire 52 extends between the coherent acoustic source 12 and a vector network analyzer 54 and a second wire 56 extends between the vector network analyzer 54 and the acoustic detector 40, to provide an electrical communication between these components. The role of the vector network analyzer 54 is to measure the amplitude and phase information of the coherent acoustic beam 14 and received scattered beams 36. It includes a built-in signal generator. To do this, the vector network analyzer 54 is electronically connected using the first and second wires 52, 56 that communicate with the coherent acoustic source 12 and the acoustic detector 40, respectively. The vector network analyzer 54 also functions as a temporal filter. The spatial filter 21 and the temporal filter restrict the volume of the acoustic virtual source 34 used for imaging, with the smaller the volume, the better the resolution for imaging. In all embodiments, the method of imaging does not require the spatial filter and can rely solely on the temporal filter, which restricts the period of time for collecting intensity from the focused virtual source 34. Without being bound to theory, the spatial filter 21 provides higher quality images in some cases but it also reduces the intensity collected by the detector(s), which, for some cases, can degrade the image. Only the volume of the beam 14 defined by either the one filter or both filters is used for detection.

The spatial resolution is set by the size of the convergent beam 30 at the focused virtual source 34. The object is always out-of-focus and is only observed in-focus upon combining all of the amplitudes and phases of the points defining the object in proper x, y, i registry.

Figure 2:
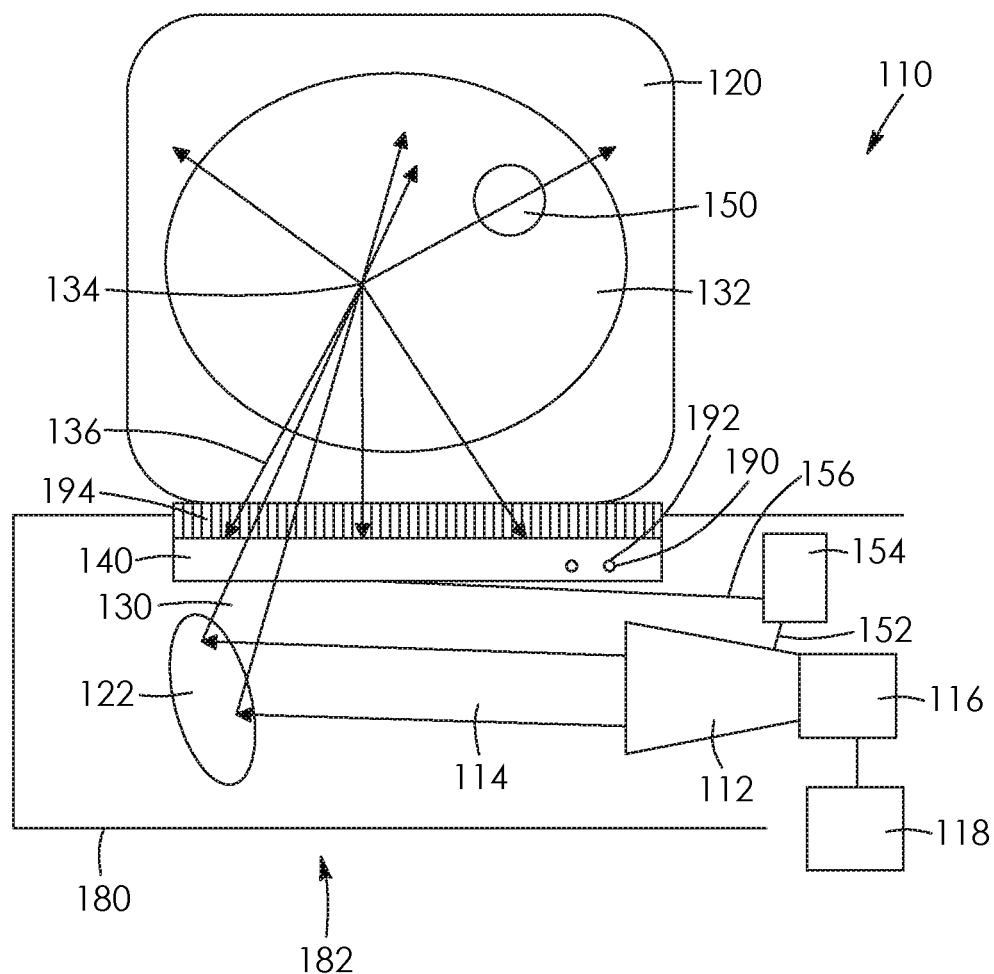
FIG. 2 is a Diffuse Acoustic Confocal imager in accordance with a second embodiment of the technology with a one or two-dimensional area detector replacing the point detector.

FIG. 2 shows an illustration of a diffuse acoustic confocal imager 110 according to a second embodiment of the present technology having the acoustic detector 40 replaced by a two-dimensional acoustic array detector 140. The acoustic detector 140, the coherent acoustic source 112, and the focusing mirror 122 are housed in a tube 180 to provide a wand style acoustic borescope or endoscope, generally referred to as 182. Again, the coherent acoustic source 112 such as a coherent acoustic emitter emits a coherent acoustic beam 114. The coherent acoustic source 112 can be manually moved or can be moved with a source actuator 116 that is in mechanical communication with the coherent acoustic source 112. The source actuator 116 is preferably controlled by a processor 118, configured to direct the source actuator 116 to cause the coherent: acoustic source 16 to scan the coherent acoustic beam 114 over the tissue or organ or object material 120. The coherent acoustic source 112 provides a coherent acoustic beam 114 with a beam frequency between about 0.5 megahertz and about 100 megahertz for obtaining information including one or more of density, temperature, composition, elasticity, or strain field in a mammalian body.

As for the first embodiment, the coherent acoustic beam 114 has a large cross sectional area, typically on the order of a centimeter or centimeters. The coherent acoustic beam 114 passes to a focusing mirror 122 where it is reflected by a curved surface and focused into a convergent beam 130 that penetrates the object medium 120 that transmits the convergent beam 130 into a first object, structure, medium or different physical state of the material or medium 132 in the object medium 120. The convergent beam 130 converges and is focused to a virtual source 134 at the point of cross-over. From the virtual source 134, the incoming convergent beam 130 is scattered in all directions three-dimensionally. The scattered beams 136 pass out of the first object 132 and the object medium 120 and are detected by a two-dimensional acoustic array detector 140. The two-dimensional acoustic array detector 140 need not be focused on the virtual source 134 and therefore need not move to collect scattered beams 136. The scattered beams 136 contain information about the object medium 120 and the first object 132 and are commonly referred to as the object beams. The resulting information carried by the scattered beams 136 is analyzed to determine its amplitude and phase according to techniques known in the art. Only those beams 136 reaching the one-dimensional or two-dimensional acoustic array detector 140 within a given and set time frame corresponding to the intensity from the virtual source 134 are used.

In order for the entire first object 132 to be observed, the virtual source 134 scans outside and inside the first object 132 by pivoting the focusing mirror 122 and the two dimensional acoustic array detector 140. Scanning of the first object 132 is also achieved by either shifting the first object 120 or shifting the microscope 110. By these means, a second object(s) 150 within the first object 132 can be imaged using the amplitude and phase information provided by the scattered beams 136 collected by the acoustic detector 140.

A first wire 152 extends between the coherent acoustic source 12 and a vector network analyzer 154 and a second wire 156 extends between the vector network analyzer 154 and two-dimensional acoustic array detector 140, to provide an electrical communication between these components. More specifically, individual wires 190 are attached to each element 192 of the two dimensional acoustic array detector 140. Each detector element 192 has its own spatial filter 194. The role of the vector network analyzer 154 is to in measure the amplitude and phase information of the emitted and received intensities. It includes a built-in signal generator. It also functions as a temporal filter.

Figure 3:
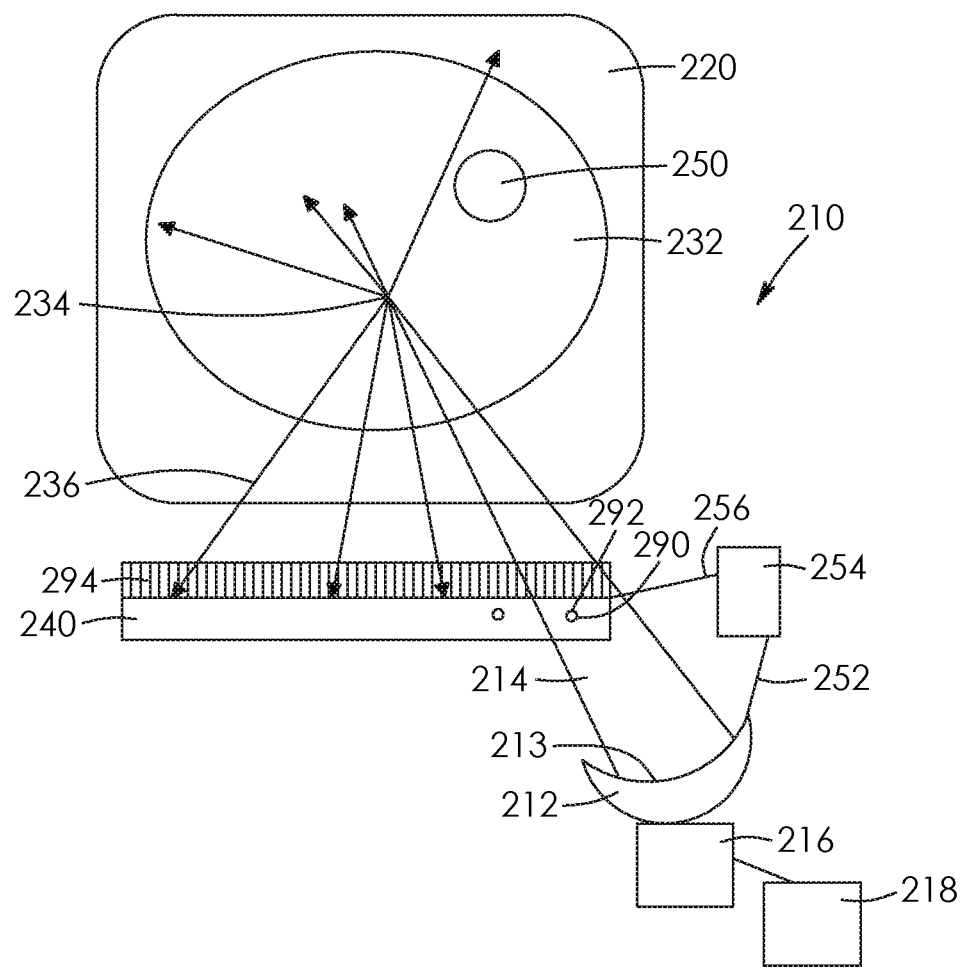
FIG. 3 is a Diffuse Acoustic Confocal Imager in accordance with a third embodiment of the technology.

FIG. 3 shows an illustration of a diffuse acoustic confocal imager 210 according to a third embodiment of the present technology. Again, the coherent acoustic source 212 such as a coherent acoustic emitter emits a coherent acoustic beam 214. The coherent acoustic source 212 can be manually moved or can be moved with a source actuator 216 that is in mechanical communication with the coherent acoustic source 212. The source actuator 216 is preferably controlled by a processor 218, configured to direct the source actuator 216 to cause the coherent acoustic source 216 to scan the coherent acoustic beam 214 over the tissue or organ or object material 220. The coherent acoustic source 212 provides a coherent acoustic beam 214 with a beam frequency between and including about 0.5 megahertz and about 100 megahertz for obtaining information including one or more of density, temperature, composition, elasticity, or strain field in a mammalian body.

As for the first embodiment, the coherent acoustic beam 214 has a large cross sectional area, typically on the order of centimeters. The coherent acoustic beam 214 passes through the surrounding acoustically transparent medium 220 such as water and into an acoustically transparent object 232 (the first object). The coherent acoustic source 212 has its emission surface 213 shaped to focus the coherent acoustic beam 214 to a virtual source 234 at the point of cross-over. From the virtual source 234, the coherent acoustic beam 214 is scattered in all directions three-dimensionally. The scattered beams 236 pass out of the first object 232 and the object medium 220 and are detected by the two-dimensional acoustic array detector 240. The one or two-dimensional acoustic array detector 240 need not be focused on the virtual source 234 and therefore need not move to collect scattered beams 236. The scattered beams 236 contain information about the object medium 220 and the first object 232 and are commonly referred to as the object beams. The resulting information carried by the scattered beams 236 is analyzed to determine its amplitude and phase according to techniques known in the art, In order for the entire first object 232 to be observed, the virtual source 234 scans outside and inside the first object 232 by pivoting the coherent acoustic source 212. Scanning of the first object 232 is also achieved by either shifting the first object 220 or shifting the microscope 210. By these means, a second object(s) 250 within the first object 232 can be imaged using the amplitude and phase information provided by the scattered beams 236 collected by the two dimensional acoustic array detector 240.

A first wire 252 extends between the coherent acoustic source 212 and a vector network analyzer 254 and a second wire 256 extends between the vector network analyzer 254 and two-dimensional acoustic array detector 240, to provide an electrical communication between these components. More specifically, individual wires 290 are attached to each element 292 of the two dimensional acoustic array detector 240. Each detector element 292 has its own spatial filter 294. The role of the vector network analyzer 254 is to in measure the amplitude and phase information of the emitted and received intensities, it includes a built-in signal generator, it also functions as a temporal filter.

The spatial resolution is set by the size of the coherent acoustic beam 214 at the focused virtual source 234 in the third embodiment. The object is always out-of-focus and is only observed in-focus upon combining all of the amplitudes and phases of the points defining the object in proper x, y, z registry.

Figure 4:
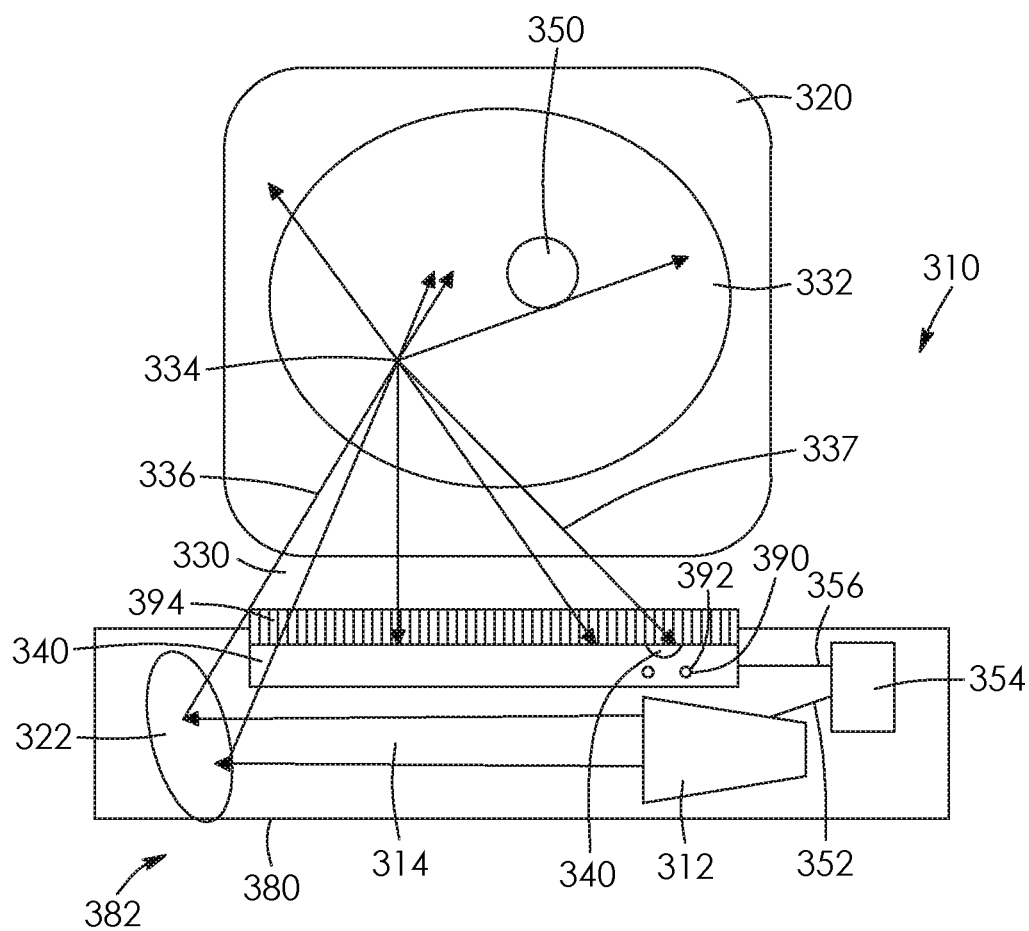
FIG. 4 is a Diffuse Acoustic Confocal Imager in accordance with a fourth embodiment of the technology.

FIG. 4 shows an illustration of a fourth embodiment of the technology. A coherent acoustic source 312 such as a coherent acoustic actuator emits a coherent acoustic beam 314. The acoustic detector 340, the coherent acoustic source 312, and the focusing mirror 322 (which is preferably flexible) are housed in a tube 380 to provide a wand style acoustic borescope, generally referred to as 382. Again, the coherent acoustic source 312 such as a coherent acoustic emitter emits a coherent acoustic beam 314. The coherent acoustic source 312 can be manually moved or can be moved with a source actuator 316 that is in mechanical communication with the coherent acoustic source 312. The source actuator 316 is preferably controlled by a processor 318, configured to direct the source actuator 316 to cause the coherent acoustic source 316 to scan the coherent acoustic beam 314 over the tissue or organ or object material 320. The coherent acoustic source 312 provides a coherent acoustic beam 314 with a beam frequency between and including about 0.5 megahertz and about 100 megahertz for obtaining information including one or more of density, temperature, composition, elasticity, strain field, magnetic or electrostatic fields in a mammalian body.

As for the first embodiment, the coherent acoustic beam 314 has a large cross sectional area, typically on the order of a centimeter or centimeters. The coherent acoustic beam 314 passes to the focusing mirror 322 where it is reflected by a curved surface and focused into a convergent beam 330 that penetrates the object medium 320 that transmits the convergent beam 330 into a first object, structure, medium or different physical state of the material or medium 332 in the object medium 320. The convergent beam 330 converges and is focused to a virtual source 334 at the point of cross-over. From the virtual source 334, the incoming convergent beam 330 beam is scattered in all directions three-dimensionally. The scattered beams 336 pass out of the first object 332 and the object medium 320. Only those beams 336 within a given and set time frame corresponding to the virtual source intensity are used. These beams are referred to as information beams 337 and are detected by a one- or two-dimensional acoustic array detector 340 with a temporal synthetic aperture. The one- or two-dimensional acoustic array detector 340 with the temporal synthetic aperture need not be focused on the virtual source 334 and therefore need not move to collect scattered beams 336. The information beams 337 contain information about the object medium 320 and the first object 332 and are commonly referred to as the object beams. The resulting information carried by the information beams 337 is analyzed to determine its amplitude and phase according to techniques known in the art.

In order for the entire first object 332 to be observed, the virtual source 334 scans outside and inside the first object 332 by pivoting the focusing mirror 32.2. and the two-dimensional acoustic array detector 340 with a temporal synthetic aperture. Scanning of the first object 332 is also achieved by either shifting the first object 320 or shifting the microscope 310. By these means, a second object(s) 350 within the first object 332 can be imaged using the amplitude and phase information provided by the information beams 337 collected by the two-dimensional acoustic array detector 340 with a temporal synthetic aperture.

A first wire 352 extends between the coherent acoustic source 332 and a vector network analyzer 354 and a second wire 356 extends between the vector network analyzer 354 and two-dimensional acoustic array detector 340 with a temporal synthetic aperture 340, to provide an electrical communication between these components. More specifically, individual wires 390 are attached to each element 392 of the two dimensional acoustic array detector 340. Each detector element 392 has its own spatial filter 394. The temporal synthetic aperture of the two-dimensional acoustic array detector 340 is used to detect or accept only the intensity emitted from the focused virtual source and to ignore the intensity scattered before the focused virtual source and the intensity scattered after the focused virtual source. The role of the vector network analyzer 354 is to in measure the amplitude and phase information of the emitted and received intensities, it includes a built-in signal generator. The temporal filter may be integral with the vector network analyzer 354.

Figure 5:
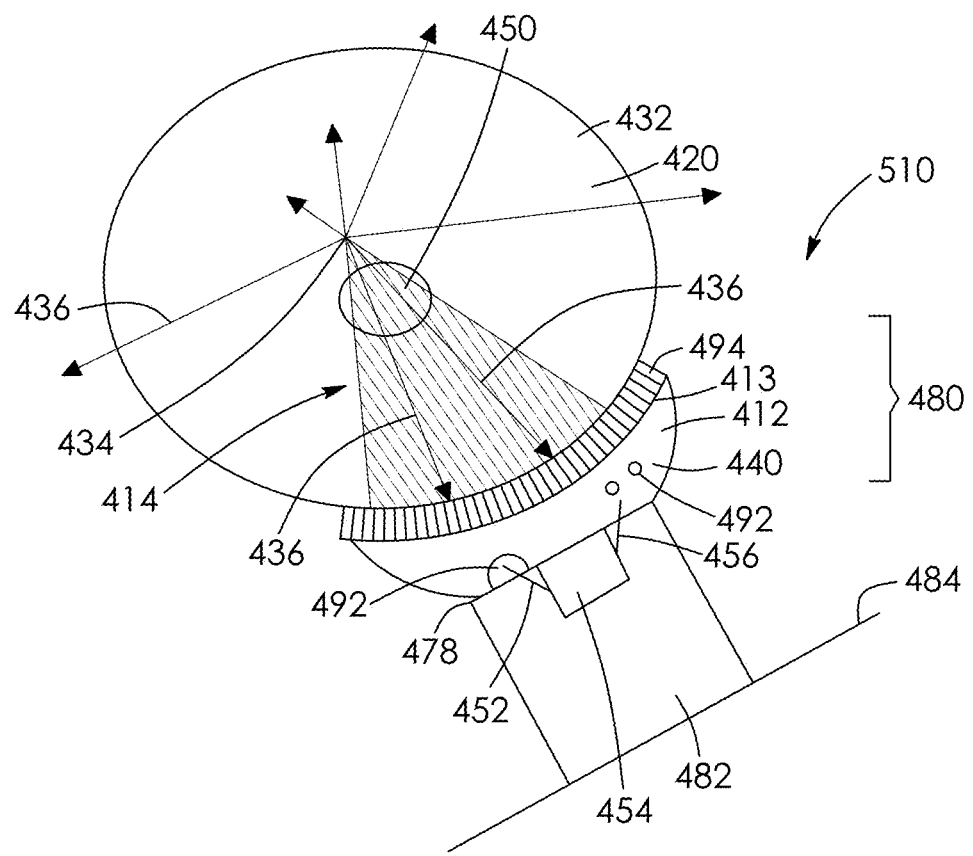
FIG. 5 is a Diffuse Acoustic Confocal Imager in accordance with a fifth embodiment of the technology.

A fifth embodiment of the technology is shown in FIG. 5. This embodiment is specially designed for diagnosis and treatment of prostate diseases and can also be used as an endoscope. The coherent acoustic source 412 and a one or two-dimensional acoustic: array detector 440 are integrated into a single combined unit 480 that is the shape of a cup that fits over the prostate and is attached to the end 478 of a wand 482. The combined unit 480 can consist of a transparent plastic lens, made of, for example, but not limited to as polymethylpentene, bonded onto a one- or two-dimensional acoustic array detector 440. The coherent acoustic source 412 has its emission surface 413 shaped to focus the coherent acoustic beam 414 to a virtual source 434 at the point of cross-over. From the virtual source 434, the coherent acoustic beam 414 is scattered in all directions three-dimensionally. The scattered beams 436 pass out of the first object 432 and the object medium 420 and are detected by the two-dimensional acoustic array detector 440. The combined unit 480 can translate and rotate using a translational+rotational stage 484. The translation and rotation of the combined unit 480 is used to move the virtual source 434.

In order for the entire first object 432 to be observed, the virtual source 434 scans outside and inside the first object 432 by pivoting the combined unit 480 using the translational and rotational stage 484. By this means, a second object(s) 450 within the first object 432 can be imaged using the amplitude and phase information provided by the scattered beams 436 collected by the two dimensional acoustic array detector 440.

A first wire 452 extends between the coherent acoustic source 412 and a vector network analyzer 454 and a second wire 456 extends between the vector network analyzer 454 and two-dimensional acoustic array detector 440, to provide an electrical communication between these components. More specifically, individual wires are attached to each element 492 of the two dimensional acoustic array detector 440. The role of the vector network analyzer 454 is to in measure the amplitude and phase information of the emitted and received intensities. It includes a built-in signal generator. It may also function as a temporal filter.

By detecting the amplitude and phase of many scattered beams 436 from many positions of the virtual source 434, the position and size of the object, for example a tumour 450, within the first object 432, for example, a prostate, can be determined. By measuring the phase of the scattered beams 436 the speed of sound of the second object 450 in the first object; 432 can be determined. The speed of sound of the second object 450 within the first object 432 can be used for diagnostic purposes.

The emitter 50 and detector 52 are made out of the same material, i.e., piezoelectric material. Therefore, by shaping the emission side of the emitter and detector unit 480 like a focusing lens, it will focus the coherent acoustic beam 414 into the first object 432(prostate) like the focusing lens and detect the scattered beams 436 using the two dimensional acoustic array detector 440 on its surface. The two dimensional acoustic array detector 440 comprises many small elements 492 on its surface where each element 492 detects independently and is a device within itself. Additionally, each detector element 492 can emit as well as detect. This allows for identification of a diseased region followed immediately by treatment of the diseased region—there is no need for equipment change, moving of the equipment—the device remains in the same location and the intensity of the coherent acoustic beam 414 is increased. Each detector element 492 has its own spatial filter 494.

Figure 6:
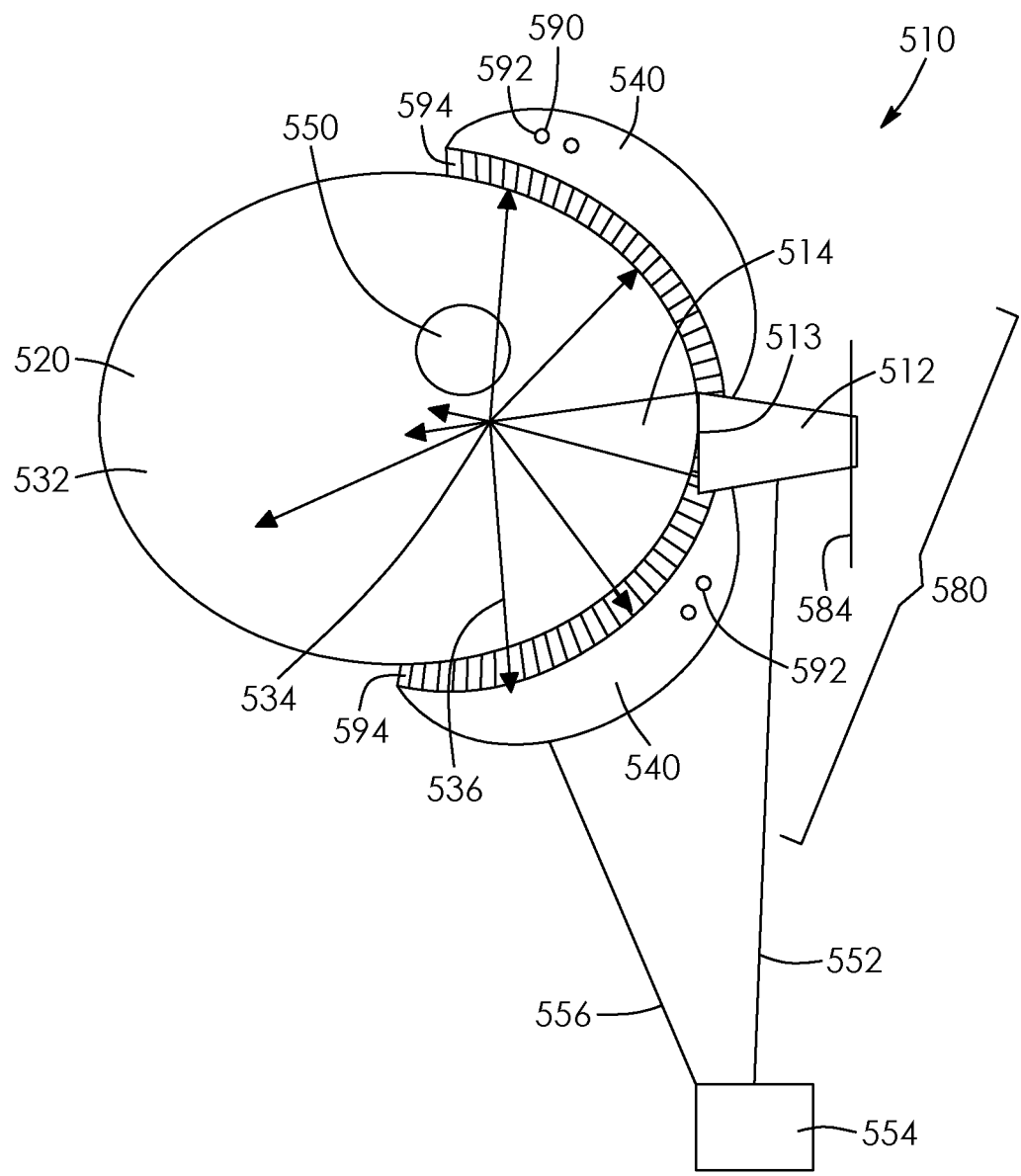
FIG. 6 is a Diffuse Acoustic Confocal Imager in accordance with a sixth embodiment of the technology.

A sixth embodiment is shown in FIG. 6. This embodiment is specially designed for diagnosis and treatment of diseases of the breast. The coherent acoustic source 512 and a two-dimensional acoustic array detector 540 are integrated into a single combined unit 580 that is the shape of a cup that fits over the breast. The coherent acoustic source 512 has its emission surface 513 shaped to focus the coherent acoustic beam 514 to a virtual source 534 at the point of cross-over. From the virtual source 534, the coherent acoustic beam 514 is scattered in all directions three-dimensionally. The scattered beams 536 pass out of the first object 532 and the object medium 520 and are detected by the two-dimensional acoustic array detector 540 with a temporal synthetic aperture that allows only those beams 536 within a given and set time frame corresponding to the virtual source intensity are used. The combined unit 580 can translate and rotate using a translational+rotational stage 584. The translation and rotation of the combined unit 580 is used to move the virtual source 534.

In order for the entire first object 532 to be observed, the virtual source 534 scans outside and inside the first object 532 by pivoting the combined unit 580 using the translational and rotational stage 584. By this means, a second object(s) 550 within the first object 532 can be imaged using the amplitude and phase information provided by the scattered beams 536 collected by the two dimensional acoustic array detector 540.

A first wire 552 extends between the coherent acoustic source 512 and a vector network analyzer 554 and a second wire 556 extends between the vector network analyzer 554 and two-dimensional acoustic array detector 540, to provide an electrical communication between these components. More specifically, individual wires are attached to each element 592 of the two dimensional acoustic array detector 540. Each detector element has its own spatial filter 594. The role of the vector network analyzer 554 is to in measure the amplitude and phase information of the emitted and received intensities. It includes a built-in signal generator. It may also function as a temporal filter.

By detecting the amplitude and phase of many scattered beams 536 from many positions of the virtual source 534, the position and size of the object, for example a tumour 550, within the first object 532, for example, a breast, can be determined. By measuring the phase of the scattered beams 536 the speed of sound of the second object 550 in the first object: 532 can be determined. The speed of sound of the second object 550 within the first object 532 can be used for diagnostic purposes.

Figure 7:
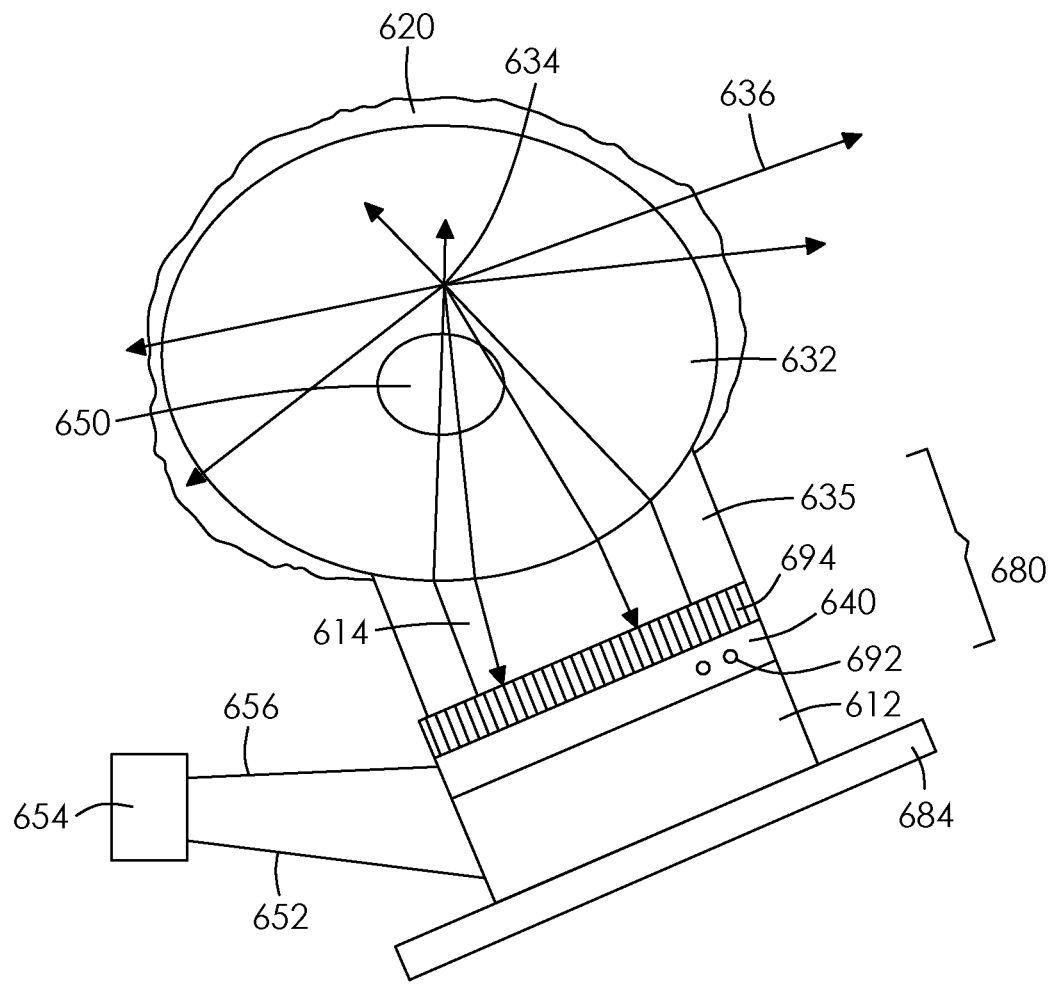
FIG. 7 is a Diffuse Acoustic Confocal Imager in accordance with a seventh embodiment of the technology.

A seventh embodiment is shown in FIG. 7. The coherent acoustic source 612, lens 635 and a one or two-dimensional acoustic array detector 640 are integrated into a single combined unit 680 that is the shape of a cup. The lens 635 may be made of, for example, but not limited to as polymethylpentene, bonded onto the one- or two-dimensional acoustic array detector 640. The lens 635 is shaped to focus the coherent acoustic beam 614 to a virtual source 634 at the point of cross-over. Note that the arrangement of the source 612 below the detector 640 can be reversed, however, the sensitivity of detection of the acoustic beam will be reduced. From the virtual source 634, the coherent: acoustic beam 614 is scattered in all directions three-dimensionally. The scattered beams 636 pass out of the first object 632 and the object medium 620 and are detected by the one or two-dimensional acoustic array detector 640.

In order for the entire first object 532 to be observed, the virtual source 634 scans outside and inside the first object 632 by pivoting the combined unit 680 using the translational and rotational stage 684. By this means, a second object(s) 650 within the first object 632 can be imaged using the amplitude and phase information provided by the scattered beams 636 collected by the one or two dimensional acoustic array detector 640.

A first wire 652 extends between the coherent acoustic source 612 and a vector network analyzer 654 and a second wire 656 extends between the vector network analyzer 654 and two-dimensional acoustic array detector 640, to provide an electrical communication between these components. More specifically, individual wires are attached to each element 692 of the two dimensional acoustic array detector 640. Each element 692 has its own spatial filter 694. The role of the vector network analyzer 654 is to in measure the amplitude and phase information of the emitted and received intensities. It includes a built-in signal generator. The vector network analyzer and its connection to the coherent acoustic source and the acoustic area detector (one or two dimensional) obviates the need for a reference or interference beam. The vector network analyzer 654 may also function as a temporal filter.

Figure 8B:
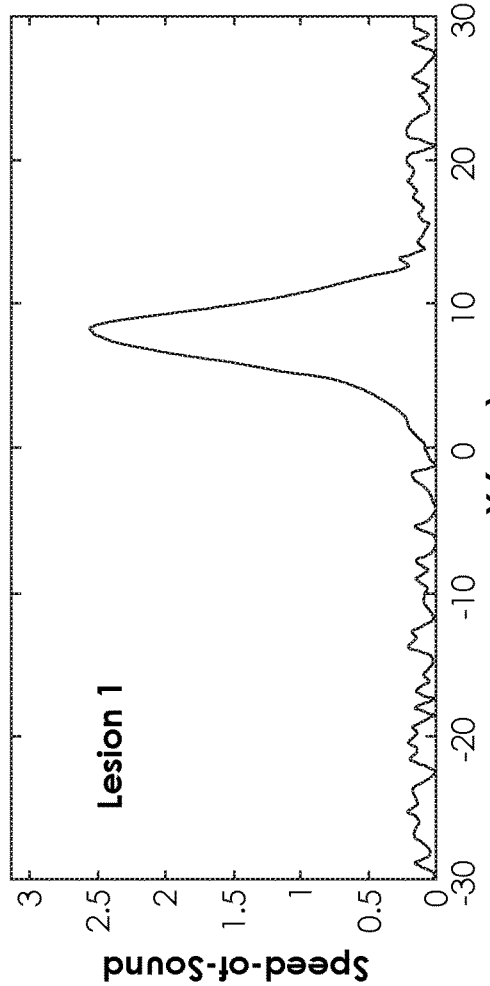
FIG. 8B shows a graphical representation of the results for lesion 1 of FIG. 8A.
Figure 8C:
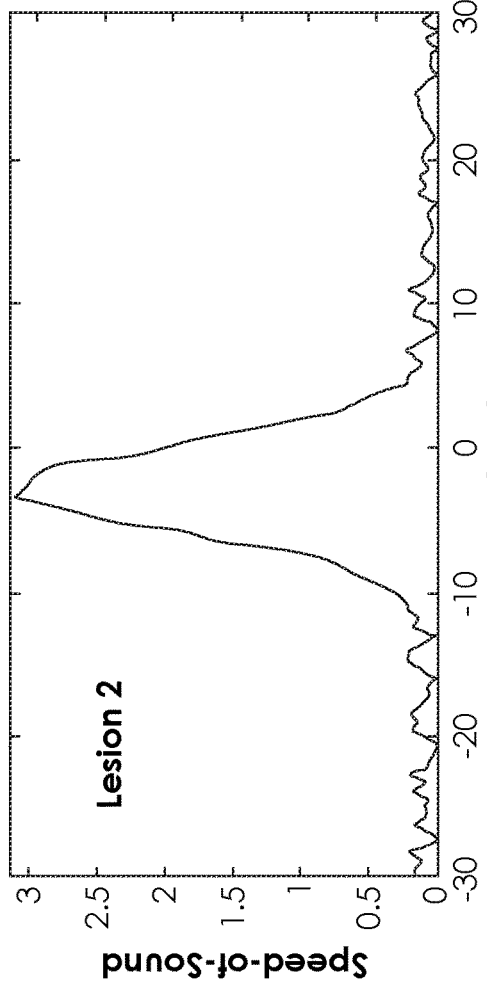
FIG. 8C shows a graphical representation of the results for lesion 2 of FIG. 8A.
Figure 8A:
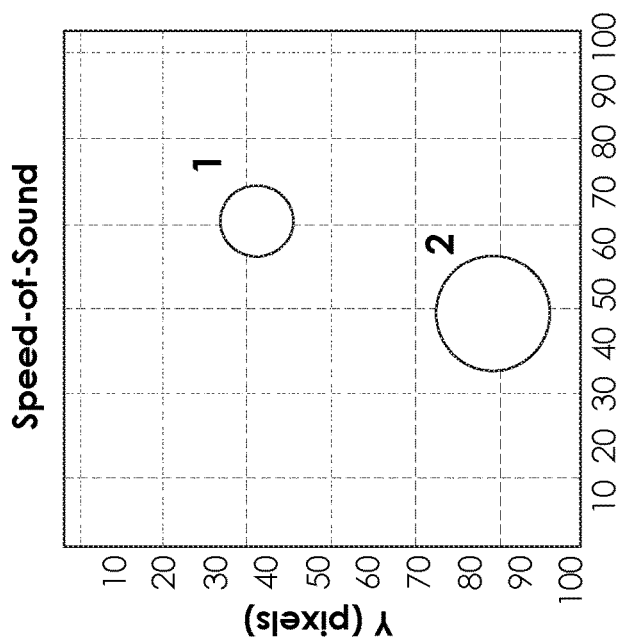
FIG. 8A shows the results obtained using the Diffuse Acoustic Confocal Imager of the present technology.

By detecting the amplitude and phase of many scattered beams 636 from many positions of the virtual source 634, the position and size of the object, for example a tumour 650, within the first object 632, for example, a prostate, can be determined. By measuring the phase of the scattered beams 636 the speed of sound of the second object 650 in the first object 632 can be determined. The speed of sound of the second object 650 within the first object 632 can be used for diagnostic purposes. An example of this is shown in FIG. 8. The size of lesion 1 is less than the size of lesion 2, as shown by the image. When this is graphed, the speed of sound allows for the size of the mass to be shown, with lesion 1 being smaller than lesion 2.

Figure 9:
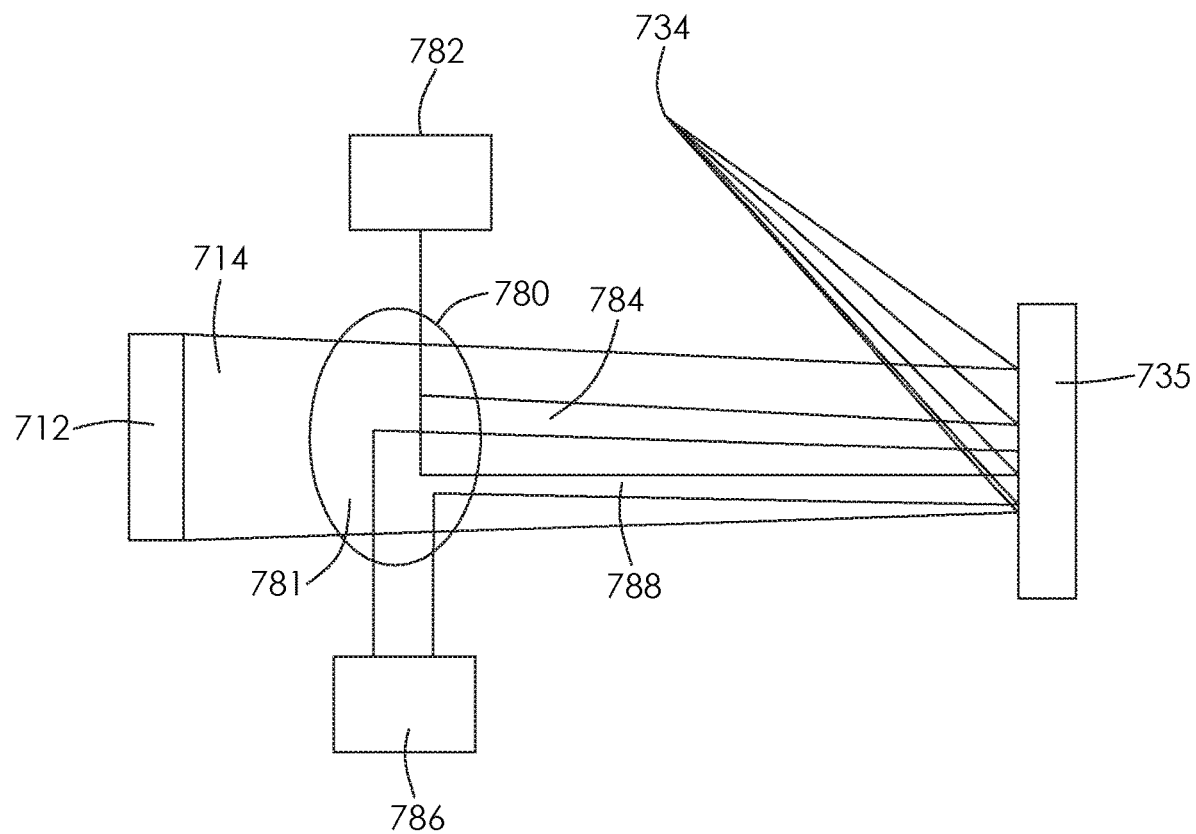
FIG. 9 shows a portion of the Diffuse Acoustic Confocal imager in accordance with any of the embodiments, wherein additional beams sources are provided.

As shown in FIG. 9, additional beams can be focused to the same location as the acoustic beam 714, as the focused virtual source 734 position is independent of wavelength. The acoustic beam 714 is emitted from the acoustic beam emitter 712. A helium-neon laser emitter 782 produces a yellow beam 784 that can be used to cauterize. It can also be used to identify the location of the focused acoustic beam 714 on the surface of the body. An infrared laser emitter 786 produces an infrared beam 788 that can be used to heat-kill tissue or ablate the tissue. The combination of the infrared beam 788 with acoustic beam allows for treatment of skin cancer with the infrared laser emitter 786, as the acoustic beam can be used to report on temperature of the skin. A mirror 780 reflects the beams 784, 788 so as to be aligned with the acoustic beam 714 as they strike the lens 735. A second mirror 781 may also be used to switch beam sources on the fly. Alternatively a roundish or elliptical mirror with a flat surface can be used and rotated around to switch beam sources on the fly. Without being bound to theory, the mirror 780 can remove coma and spherical aberrations. If a specific and narrow wavelength of beam is used, chromatic aberrations can also be removed. Note that only a portion of the device is shown in this figure so as to clearly show the significant changes. All components in the previous embodiments are found in this embodiment.

Figure 10:
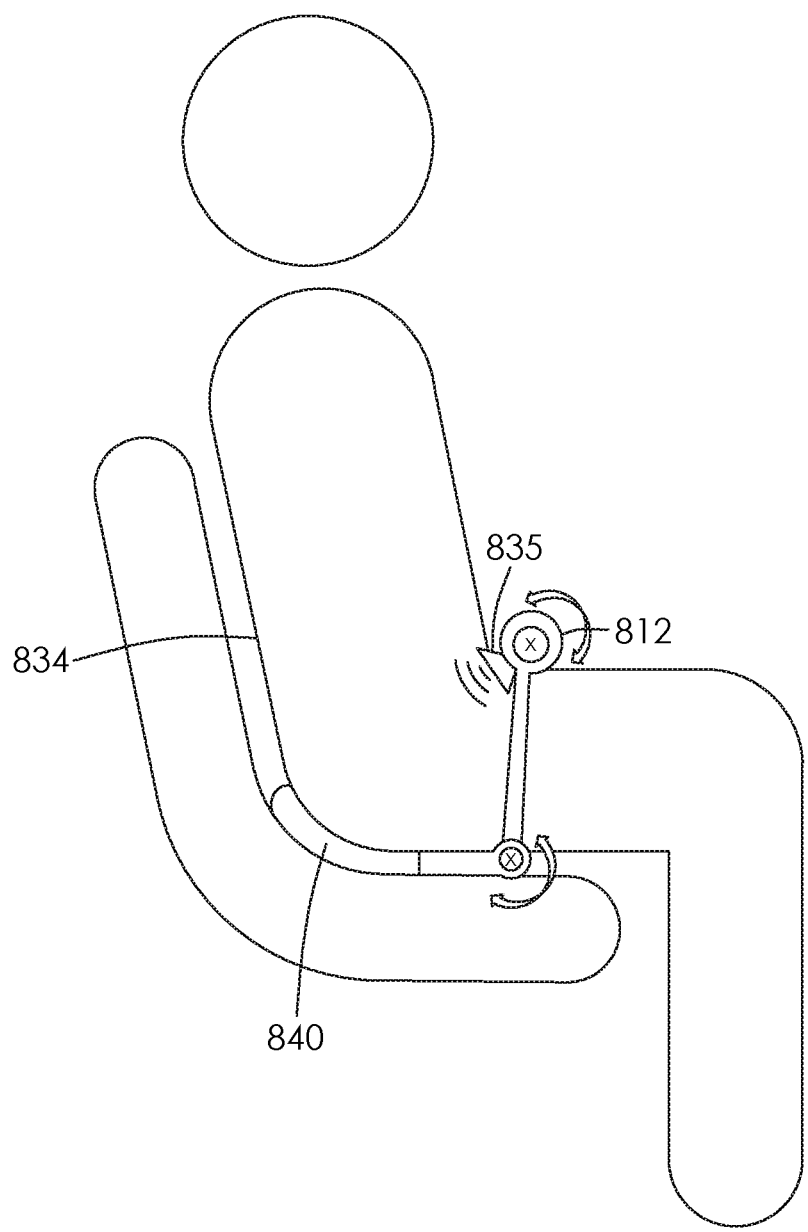
FIG. 10 shows a portion of the Diffuse Acoustic Confocal Imager, wherein the Imager is configured for non-invasive diagnosis and treatment of prostate cancer and other conditions of the prostate treatable with the imager of the present technology.

As shown in FIG. 10, the beam emitter 812 and the lens 835 work in unison. For detection and treatment of prostate cancer, the acoustic beam is focused in the bladder of the patient 834. The focused virtual source scatters through the prostate and is detected by the detector 840. The detector 840 is shaped to allow a patient to sit on it. Note that only the components that differ from the preceding embodiments are shown in this figure. All components in previous embodiments are found in this embodiment.

Figure 11:
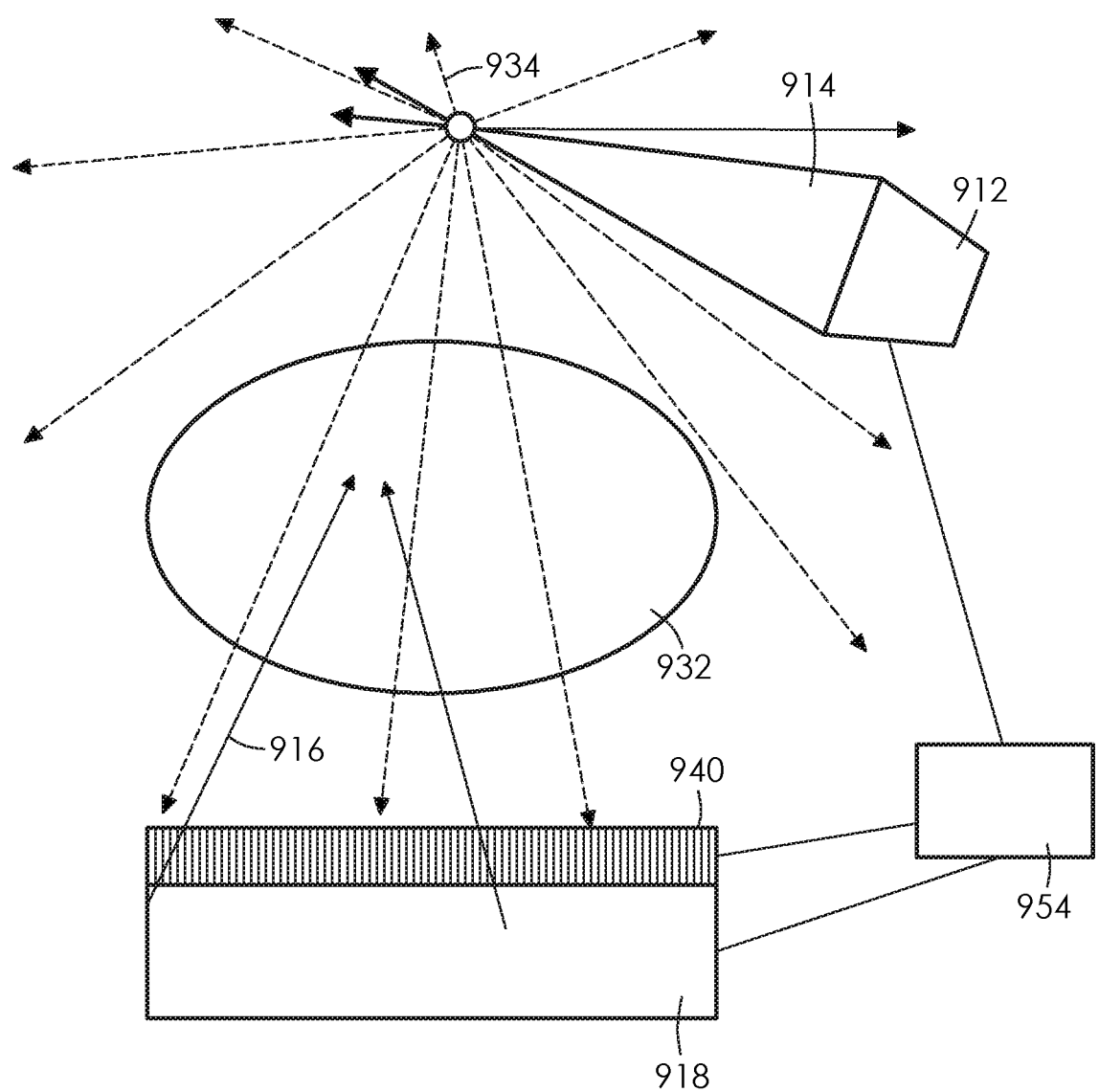
FIG. 11 shows another embodiment of the present technology wherein two acoustic beam emitters are employed to determine functioning of an object.

As shown in FIG. 11, two acoustic beam emitters are used in unison. The first acoustic beam emitter 912 emits the first acoustic beam 914, and the second acoustic beam 916 is emitted from the second acoustic beam emitter 918. The second acoustic beam emitter 918 is located below the linear array detector 940. The vector network analyzer 954 is configured as described above. Al the components described in previous embodiments are found in this embodiment. The first beam 914 is focused to provide the virtual source 934, which then sends the scattered beams to the object to permit imaging, as described above. The second acoustic beam 916 is focused on the object 932 to stimulate the prostrate. This allows for determining functional abnormalities, in the preferred embodiment, the object is the prostate.

Figure 12:
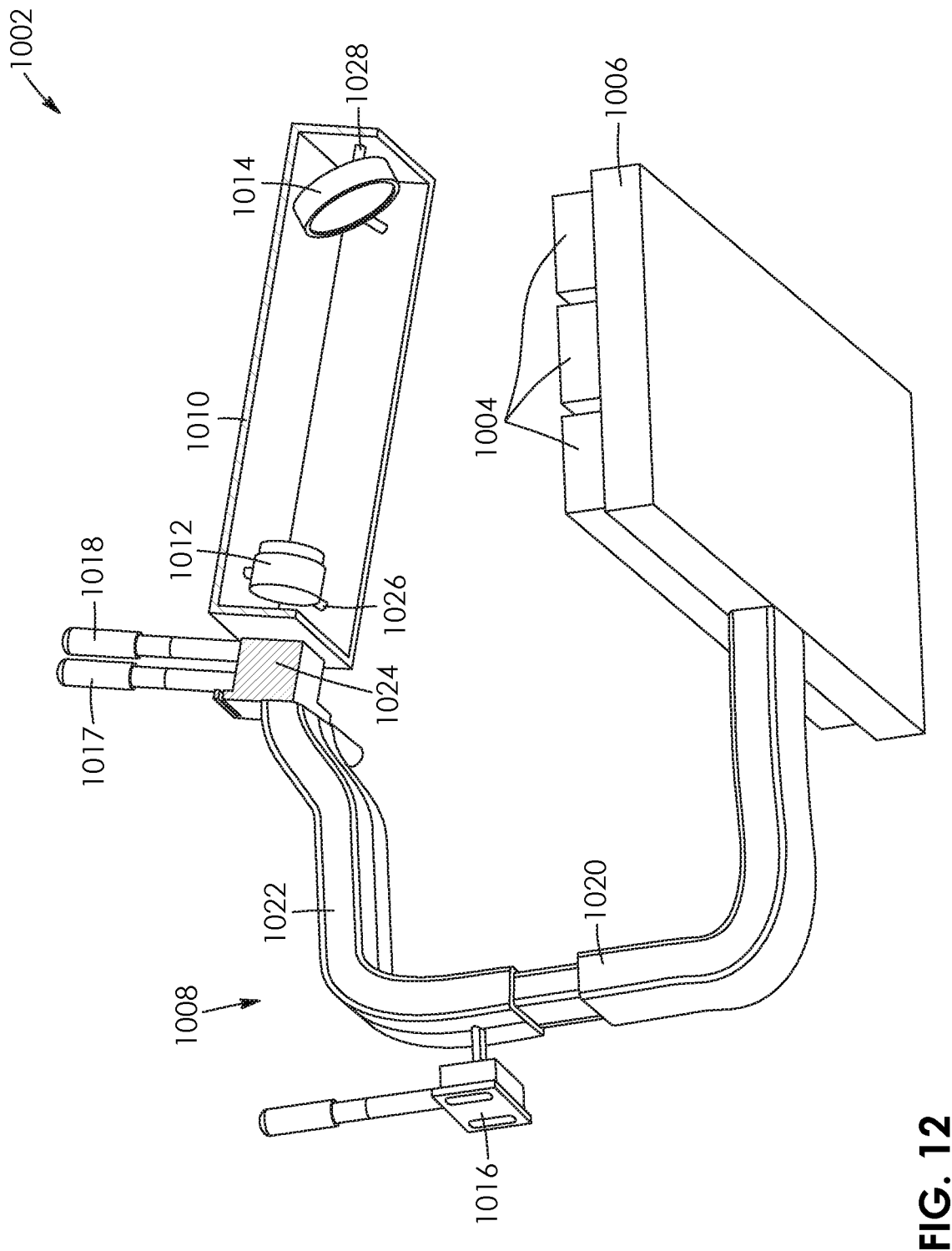
FIG. 12 shows a schematic of a unit for imaging the prostate non-invasively.

An alternative embodiment of the DACI design, generally referred to as 1002, for imaging and treating the prostate, is shown in FIG. 12. This is an overview of the design. The design includes all the components as described above, whether shown or not. The acoustic detector 1004 is located on a platform 1006. An adjustable arm 1008 extends from and is attached to the acoustic detector 1004 at one end and to a housing 1010 that houses the coherent acoustic source 1012 and the focusing mirror 1014. Three gantry attachments 1016, 1017, 1018 are attached to the adjustable arm 1008 to position the device 1002 on the person or alternatively, three gantries are above the device to adjust the position of the patient. One gantry 1016 allows for length adjustment as the adjustable arm 1008 has a first section 1020 that is telescopically engaged to the second section 1022. The second and third gantry 1017, 1018 control rotation of the housing 1010 about the adjustable arm 1008. A suitable pivot joint 1024 connects the housing 1010 to the adjustable arm 1008. Two actuators (goniometers) 1026, 1028 are under control of a computing device and are used to ensure that the beam is correctly focused and to allow for imaging in the three dimensions. One controls positioning of the detector and the other controls positioning of the source. Note that the focusing mirror can be replaced with a focusing lens. The detector 1004 is anticipated to be about 10 cm×10 cm in area. A vector network analyzer in electronic communication with each of the coherent acoustic source and the acoustic detector.

Figure 13:
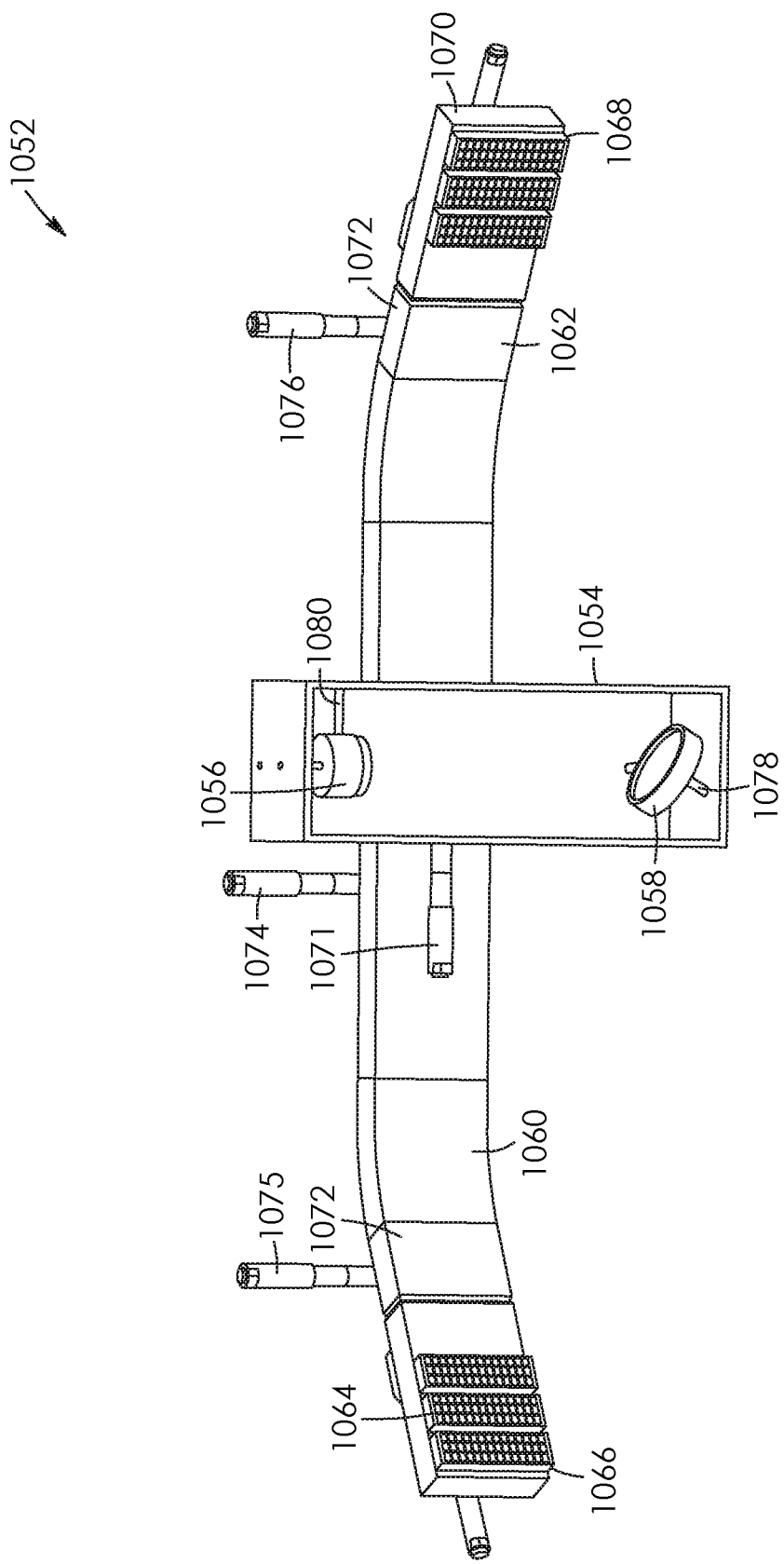
FIG. 13 shows a schematic of a unit for imaging the ovaries non-invasively.

An alternative embodiment of the DACI design, generally referred to as 1052, for imaging and treating the ovaries, is shown in FIG. 13. This is an overview of the design. The design includes all the components as described above, whether shown or not. A housing 1054 houses the coherent acoustic source 1056 and the focusing mirror 1058. It is attached to two adjustable arms 1060, 1062. A first detector 1064 is at the end 1066 or in the vicinity of the end 1066 of the first arm 1060 and a second detector 1068 is at the end 1070 of the second arm 1062 or in the vicinity of the end 1070. The arms 1060, 1062 are slidably engaged with one another with a slider 1071 or with the housing 1054 to allow for length adjustment. The arms 1060, 1062 include hinges 1072 in communication with three gantries 1074, 1075 1076 or the gantries are located above the device to position the patient. In an alternative embodiment, the arms 1060, 1062 are made of a flexible strap that allows for infinite adjustment to allow the detectors to be placed over the ovaries. Three actuators 1078, 1079, 1080 are under control of a computing device and are used to ensure that the beam is correctly focused and to allow for imaging in the three dimensions, hence two control the detector positions and one controls the source position. A vector network analyzer in electronic communication with each of the coherent acoustic source and the acoustic detectors. Note that the focusing mirror can be replaced with a focusing lens.

Example 1

The effectiveness of the device and system was demonstrated using a prostate elastography phantom containing three randomly placed isoechoic lesions from CSP Medical that are three times harder than the simulated prostate tissue, as shown in FIG. 8 Four acoustic phase images were taken at scan depths from 10 mm to 25 mm in which the margins of the prostate and the margin of the urethra, bright orange to bright yellow coloring, could be identified. The ultrasound beams radiate out from the beam source and the image is collected from the diffuse beams. Regions of higher speed of sound are indicated at A and B. Using any of embodiments 1-4 and 6 of the present technology, two of the lesions were scanned. These lesions were clearly identifiable. The size, three dimensional shape, position and location could be determined. Other features of disease tissue were not present in the prostate phantom and hence, information was limited to the characteristics that were different.

Example 2

The DACI can be used in medical diagnostics to non-intrusively observe the variations in temperature within the body such as, but not limited to, within an organ, muscles, fatty tissue, cancerous tissue and at the interfaces between body organs and their surroundings. Since the DACI focuses the beam to a virtual source, which is passed quickly over a point, it can be very gentle on the body by giving a low radiation dose. The power density is generally less than 1 watt per square centimeter and dwell times of milliseconds to seconds to avoid heating and cavitation effects in the object under examination. Once the internal body can be seen by the DACI, by increasing the intensity from tens of watts to hundreds of watts per square centimeter and dwell time of the beam from seconds to hundreds of seconds, treatments become possible, using beam heating methods and tumor ablation (break-up) methods such as high intensity focused ultrasound. Since the DACI microscope can also measure temperature by determining the speed of sound of the object beams, the temperature of the region of the body being treated by beam heating can be monitored during the treatment process to help ensure a successful treatment. Additionally, the treatment can be monitored by measuring scattering intensity as it decreases with an increase in tumour ablation/break up.

Example 3

In objects comprising of plasma, gases, liquids, and solids, there are many unanswered questions to simple states of matter, such as, but not limited to the 3D temperature and the 3D composition existing within objects and at interfaces between immiscible and miscible fluids, a container and its contents, and within fluids having various states, such as within a simple flame burning fuel during combustion. The speed of sound changes as the state of matter changes. There are higher speeds of sound for stiffer, higher-elasticity materials. The application of the DACI microscope to objects transparent to acoustic beams will answer many of these questions.

Example 4

Now that radiation sources, such as acoustic beams, can be obtained having very good beam coherence, amplitude and phase images of large objects are possible, on the order of many centimeters. It will be possible with the development of new optical focusing materials transparent or reflective to acoustic beams such as plastics that may be able to observe much larger and smaller objects in the future.

Example 5

Diagnosis and treatment of prostate cancer. Prostate cancer tumours are hard and multi shaped with fine branches. Blood flow is increased around the tumour, but the hardness of the tumour prevents the blood reaching the tumour and eventually restricts blood flow around the tumour. The current state of the art is ultrasound imaging of the prostate. This provides information on the size of the gland, as only the interface between the prostate and surrounding tissue can be identified. At that, the images are not highly accurate as the diffuse scattering of the beams interferes with the image and leads to fuzzy edges.

The present technology is provided as a wand with the emitter complex and the detector holder at a distal end. As noted above, the emitters may also function as the detectors. This allows for a single complex to be used with a holder that is appropriately shaped for the body part to be imaged. Alternatively, the emitters are housed on an emitter complex that is integrated into the detector holder. Again, the shape of the holder is appropriate for the body part being imaged.

There are diseases within the body such as within the prostate, each having their own speed of sound, hence the speed of sound is a signature for each disease (see Example 6). Further, each developmental state of the disease has a signature speed of sound.

Example 6

Speed of sound will be measured for any disease or condition of interest, and for each developmental stage of the disease or condition. The present technology will be used to make this determination. The present technology will then be used to diagnose or diagnose and treat, or track progression of the disease or condition or track progression of treatment of the disease or condition. Change in speed of sound can be caused by changes in one of more of cell size, cellular granularity, tissue elasticity, blood accumulation, increase in temperature, inflammation and immune cell infiltration. Examples of different speeds of sound are 1574 m/s for smooth muscle fibres, 1610 m/s for papillary adenocarcinoma, 1610 m/s for tubular adenocarcinoma (well differentiated}, 1600 m/s for tubular adenocarcinoma (moderately differentiated), 1557 m/s for tubular adenocarcinoma (poorly differentiated) and 1523 m/s for singlet-ring cell carcinoma. Other known speeds of sound are for breast tissue, with the speed of sound of 1422 m/s for fatty tissue, 1487 m/s for breast parenchyma, 1548 m/s for a malignant lesion and 1513 m/s for a benign lesion. The standard deviation was not more than ±1.7%.

Example 7

The two dimensional acoustic array detector was replaced with a linear acoustic array detector. It was found that the focused virtual source also be created by the linear array actuator emission. The linear array actuator can focus the beam by a curved surface of a lens or it can also be focused by adjusting the relative phases of the emitting elements in the array of transducers (i.e., a "phased array"). Although the phased array can't produce a small virtual source, it can still produce a virtual source, which can be used for imaging at a lower spatial resolution.

Example 8

Using the device of FIG. 12, the gantries are used to position a patient or the device. The patient is in a warm salt bath or has an acoustic gel applied between them and the DACI interface for enhancing the passage of the acoustic beam between the DACI and the patient. The acoustic emitter and focusing mirror assembly are positioned on the outside of the body just above the pelvic bone, using the first goniometer (which is an adjustor) and the second goniometer (again, an adjustor) is used to raster the virtual source inside the bladder. The acoustic beam is focused into the bladder, which is preferentially full, to create the virtual source inside the body. From the virtual source inside the bladder, the diffusely scattered intensity passes through the prostate for imaging by the detector that the patient is sitting on. The virtual source is moved or rastered within the bladder to image the prostate from many different positions which enables a three-dimensional image of the prostate including a three-dimensional view of any diseased region. If the prostate is diseased, it can be treated as described above. Both the detection and the treatment are non-invasive.

Example 9

Using the device of FIG. 13, the gantries are used to position the patient or the device as needed. The patient is in a warm salt bath or has an acoustic gel applied between them and the DACI interface for enhancing the passage of the acoustic beam between the DACI and the patient. The acoustic emitter and focusing mirror assembly are positioned on the outside of the body just above the pelvic bone, using the first adjustor and the second adjustor is used to raster the virtual source inside the bladder. The acoustic beam is focused into the bladder, which is preferentially full, to create the virtual source inside the body. From the virtual source inside the bladder, the diffusely scattered intensity passes through the ovaries for imaging by the detector. The virtual source is moved or rastered within the bladder to image the ovaries from many different positions which enables a three-dimensional image of the ovaries including a three-dimensional view of any diseased region. If an ovary is diseased, it can be treated as described above. Both the detection and the treatment are non-invasive.

Advantages of the exemplary embodiments described herein may be realized and attained by means of the instrumentalities and combinations particularly pointed out in this written description. It is to be understood that the foregoing general description and the following detailed description are exemplary and explanatory only and are not restrictive of the claims below. While example embodiments have been described in detail, the foregoing description is in all aspects illustrative and not restrictive, it is understood that numerous other modifications and variations can be devised without departing from the scope of the example embodiment.

While example embodiments have been described in connection with what is presently considered to be an example of a possible most practical and/or suitable embodiment, it is to be understood that the descriptions are not to be limited to the disclosed embodiments, but on the contrary, is intended to cover various modifications and equivalent arrangements included within the spirit and scope of the example embodiment. Those skilled in the art will recognize, or be able to ascertain using no more than routine experimentation, many equivalents to the specific example embodiments specifically described herein. Such equivalents are intended to be encompassed in the scope of the claims, if appended hereto or subsequently filed.

What is claimed is:

1. A diffuse acoustic confocal imager device for use with a processor for providing dimensional and state information on an object based on an at least one phase image, the device comprising a phased array transducer configured to produce an acoustic coherent beam ranging from 0.5 megahertz to 100 megahertz, a lens for focusing the acoustic coherent beam to a virtual source, and a vector network analyzer, which is for measuring a phase of the acoustic confocal beam and a phase of the at least one diffusely scattered beam to provide the at least one phase image, the vector network analyzer in electronic communication with the phased array transducer, wherein the phased array transducer is also configured to detect diffusely scattered beams from the virtual source that travel through said object.

2. The device of claim 1, wherein the phased array transducer includes a spatial aperture.

3. The device of claim 2, wherein the phased array detector and the lens are integrated into a unit.

4. The device of claim 1, wherein the phased array transducer and the lens are integrated into a unit.

5. A method of imaging a tissue using a diffuse acoustic confocal imager device, based on an at least one phase image, the method comprising emitting an acoustic confocal beam of 0.5 to 100 megahertz from a phased array, focusing the acoustic confocal beam to a virtual source in the tissue, scanning the tissue with the virtual source at a low dwell time, detecting diffusely scattered beams from the virtual source that travel through said tissue with the phased array transducer, measuring a phase of the acoustic confocal beam and a phase of the diffusely scattered beams to provide the at least one phase image of the tissue.

6. The method of claim 5, further comprising analyzing the phase image to diagnose a disease in the tissue.

7. The method of claim 6, wherein the tissue is a prostate.

8. The method of claim 7 further comprising treating the disease in the prostate immediately upon diagnosing the disease.

9. The method of claim 8, further comprising treating the disease in the prostate by increasing the dwell time to a high dwell time.

10. A diffuse acoustic confocal imager device for use with a processor for providing dimensional and state information on an object based on an at least one phase image, the device comprising: a phased array transducer for producing an acoustic coherent beam ranging from 0.5 megahertz to 100 megahertz and which includes a plurality of elements and a spatial apertures for each element; a lens for focusing an acoustic coherent beam to a virtual source; and a vector network analyzer, which is for a phase of the acoustic confocal beam and a phase of diffusely scattered beams to provide the at least one phase image, the vector network analyzer in electronic communication with the phased array transducer and each element of the plurality of elements of the phased array transducer, wherein the phased array transducer is also for detecting the diffusely scattered beams from the virtual source that travel through the object.

* * * * *